United States Patent
Gustavsson

(10) Patent No.: US 8,945,105 B2
(45) Date of Patent: *Feb. 3, 2015

(54) FLUORESCENT HANDPIECE

(71) Applicant: Morgan Lars Ake Gustavsson, Newport Beach, CA (US)

(72) Inventor: Morgan Lars Ake Gustavsson, Newport Beach, CA (US)

(73) Assignee: Morgan Gustavsson, Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/075,828

(22) Filed: Nov. 8, 2013

(65) Prior Publication Data

US 2014/0194956 A1    Jul. 10, 2014

Related U.S. Application Data

(63) Continuation of application No. 13/863,260, filed on Apr. 15, 2013, now Pat. No. 8,579,951, which is a continuation of application No. 13/651,666, filed on Oct. 15, 2012, now Pat. No. 8,419,781, which is a continuation of application No. 13/361,748, filed on Jan. 30, 2012, now Pat. No. 8,287,578, which is a continuation of application No. 13/153,702, filed on Jun. 6, 2011, now Pat. No. 8,105,369, which is a continuation of application No. 12/014,989, filed on Jan. 16, 2008, now Pat. No. 7,955,367.

(51) Int. Cl.
*A61N 5/06* (2006.01)

(52) U.S. Cl.
CPC ............ *A61N 5/0616* (2013.01); *A61N 5/0613* (2013.01); *A61N 2005/0644* (2013.01)
USPC .... 606/10; 606/9; 607/88; 607/89; 250/461.1

(58) Field of Classification Search
CPC ...................... A61N 5/062; A61N 2005/0652
USPC .................. 606/9, 10; 607/88, 89; 250/461.1
See application file for complete search history.

(56) References Cited

U.S. PATENT DOCUMENTS

| | | |
|---|---|---|
| 3,426,194 A | 2/1969 | Werner |
| 3,818,129 A | 6/1974 | Yamamoto |
| 4,499,403 A | 2/1985 | Leppelmeier et al. |
| 5,026,366 A | 6/1991 | Leckrone |

(Continued)

FOREIGN PATENT DOCUMENTS

| | | |
|---|---|---|
| DE | 103 35 303 | 2/2004 |
| EP | 0 586 353 A1 | 3/1994 |

OTHER PUBLICATIONS

Gustafsson, et al., "A Variable Pulsewidth Vascular System for Dermatology," SPIE, vol. 2128:188-196 (1994).

*Primary Examiner* — William Thomson
*Assistant Examiner* — Jeffrey Lipitz
(74) *Attorney, Agent, or Firm* — Knobbe, Martens, Olson & Bear, LLP.

(57) ABSTRACT

A handpiece can treat biological tissue using electromagnetic radiation, which can be substantially fluorescent light. The handpiece includes a source of electromagnetic radiation and a waveguide. The waveguide is adjacent the source, receives electromagnetic radiation from the source, and delivers the electromagnetic radiation to the biological tissue. The handpiece also includes a system for circulating a fluorescent substance through the waveguide. The fluorescent substance is capable of modulating at least one property of the electromagnetic radiation.

20 Claims, 9 Drawing Sheets

(56) References Cited

U.S. PATENT DOCUMENTS

| | | |
|---|---|---|
| 5,320,618 A | 6/1994 | Gustafsson |
| 5,620,478 A | 4/1997 | Eckhouse |
| 5,626,631 A | 5/1997 | Eckhouse |
| 5,720,772 A | 2/1998 | Eckhouse |
| 5,755,751 A | 5/1998 | Eckhouse |
| 6,231,567 B1 | 5/2001 | Rizoiu et al. |
| 6,231,593 B1 | 5/2001 | Meserol |
| 6,235,015 B1 | 5/2001 | Mead et al. |
| 6,254,597 B1 | 7/2001 | Rizoiu et al. |
| 6,280,438 B1 | 8/2001 | Eckhouse et al. |
| 6,328,760 B1 | 12/2001 | James |
| 6,334,074 B1 | 12/2001 | Spertell |
| 6,343,174 B1 | 1/2002 | Neuberger |
| 6,350,123 B1 | 2/2002 | Rizoiu et al. |
| 6,413,268 B1 | 7/2002 | Hartman |
| 6,443,946 B2 | 9/2002 | Clement et al. |
| 6,514,243 B1 | 2/2003 | Eckhouse et al. |
| 6,693,285 B1 | 2/2004 | Weiss |
| 6,981,970 B2 | 1/2006 | Karni |
| 7,083,610 B1 | 8/2006 | Murray et al. |
| 7,112,194 B2 | 9/2006 | Fujieda |
| 7,187,822 B2 | 3/2007 | Rizoiu et al. |
| 7,208,007 B2 | 4/2007 | Nightingale et al. |
| 7,955,367 B2 | 6/2011 | Gustavsson |
| 7,998,181 B2 | 8/2011 | Nightingale et al. |
| 8,105,369 B2 | 1/2012 | Gustavsson |
| 8,287,578 B2 | 10/2012 | Gustavsson |
| 8,419,781 B2 | 4/2013 | Gustavsson |
| 8,465,532 B2 | 6/2013 | Gustavsson |
| 8,518,093 B2 | 8/2013 | Gustavsson |
| 8,579,951 B2 | 11/2013 | Gustavsson |
| 2002/0067121 A1 | 6/2002 | Jean et al. |
| 2002/0168317 A1 | 11/2002 | Daighighian et al. |
| 2003/0032950 A1 | 2/2003 | Altshuler et al. |
| 2003/0044114 A1 | 3/2003 | Pelka |
| 2006/0020309 A1 | 1/2006 | Altshuler et al. |
| 2006/0030909 A1 | 2/2006 | Karni |
| 2006/0240381 A1 | 10/2006 | Rizoiu et al. |
| 2006/0282137 A1 | 12/2006 | Nightingale et al. |
| 2007/0166663 A1 | 7/2007 | Telles et al. |
| 2008/0025672 A1 | 1/2008 | Boutoussov et al. |
| 2009/0036953 A1 | 2/2009 | Gustavsson | ns
FLUORESCENT HANDPIECE

CROSS-REFERENCE TO RELATED APPLICATIONS

This application is a continuation of U.S. application Ser. No. 13/863,260, filed Apr. 15, 2013, which is a continuation of U.S. application Ser. No. 13/651,666, filed Oct. 15, 2012, now U.S. Pat. No. 8,419,781, which is a continuation of U.S. application Ser. No. 13/361,748, filed Jan. 30, 2012, now U.S. Pat. No. 8,287,578, which is a continuation of U.S. application Ser. No. 13/153,702, filed Jun. 6, 2011, now U.S. Pat. No. 8,105,369, which is a continuation of U.S. application Ser. No. 12/014,989, filed Jan. 16, 2008, now U.S. Pat. No. 7,955,367, all of which are expressly incorporated by reference in their entireties.

BACKGROUND OF THE INVENTION

1. Field of the Invention

The invention relates generally to apparatuses and methods for treating biological tissue using electromagnetic radiation. In particular, the invention relates to a fluorescent handpiece for treating biological tissue.

2. Description of the Related Art

Certain treatments for cosmetic and dermatologic conditions include the use of non-coherent fluorescent light or intense pulsed light. For example, devices can include a fluorescent substance or dye for transforming a first predetermined wavelength band of light to a second predetermined pulsed wavelength band of light, a first light source for producing light including said first predetermined wavelength band, and a waveguide for directing said second predetermined pulsed wavelength band to a predetermined location. Unfortunately, the efficacy of the dye can suffer from quenching, bleaching, and other chemical reactions. Also, because the fluorescent substance or dye is heated during operation, and because heating can limit the useful lifetime of the dye, such devices can address the heating of the fluorescent substance or dye. For example, the dye can be circulated through a separate base unit, to mitigate quenching, bleaching, and other chemical reactions, or to cool the dye in an attempt to extend its useful lifetime. However, the volume of circulating dye can be large and the system required to store, pump, and circulate the dye can be large. Due to the volume of dye and the size of the system, these components are generally in a base unit separate from the treatment handpiece.

SUMMARY OF THE INVENTION

The invention, in various embodiments, relates to apparatuses and methods for treating biological tissue using electromagnetic radiation. The biological tissue can be human skin, which can exhibit at least one of superficial vascular lesion, port wine stain, telangiectasia, small vessel diameter lesion, arterial lesion, capillary lesion, venous lesion, pigmented lesions, tattoos and other dermatological indications such as acne, psoriasis, vitiligo, and the like. The invention can also be used to treat wrinkles, for skin rejuvenation, for hair removal, and for hair regrowth. Apparatuses can include fluorescent handpieces that include a source of electromagnetic radiation, a nonlinear waveguide, and a system for circulating a fluorescent substance through the nonlinear waveguide. Advantages of the invention can include an apparatus that can be smaller, less expensive, easier to handle, easier to store, more efficient, and more robust than prior art sources of electromagnetic radiation. Other advantages of the invention can include extending the usable lifetime of the fluorescent substance by at least one of mitigating quenching of the fluorescent substance, mitigating bleaching of the fluorescent substance, mitigating heating of the fluorescent substance, and mitigating chemical reaction of the fluorescent substance.

In one aspect, the invention features a handpiece for treating biological tissue. The handpiece includes a source of electromagnetic radiation, a nonlinear waveguide and a system for circulating a fluorescent substance through the nonlinear waveguide. The nonlinear waveguide is adjacent the source, receives electromagnetic radiation from the source, and delivers modulated electromagnetic radiation to the biological tissue. The fluorescent substance is capable of modulating at least one property of the electromagnetic radiation.

In another aspect, the invention features an apparatus for treating biological tissue. The apparatus includes a base unit, an energy source associated with the base unit, and an umbilicus. The umbilicus has a first end associated with the base unit and a conduit for transmitting energy from the energy source to a second end of the umbilicus. The apparatus also includes a handpiece associated with the second end of the umbilicus. The handpiece includes a source of electromagnetic radiation, a nonlinear waveguide, and a system for circulating a fluorescent substance through the nonlinear waveguide. The source is adapted for receiving energy from the energy source through the conduit. The nonlinear waveguide is adjacent the source, receives electromagnetic radiation from the source, and delivers modulated electromagnetic radiation to the biological tissue. The fluorescent substance is capable of modulating at least one property of the electromagnetic radiation.

In still another aspect, the invention features a method of treating biological tissue. The method includes (i) providing electromagnetic radiation to a nonlinear waveguide associated with a handpiece; (ii) circulating a fluorescent substance through the nonlinear waveguide to modulate at least one property of the electromagnetic radiation; and (iii) delivering the modulated electromagnetic radiation to treat the biological tissue.

In other examples, any of the aspects above, or any apparatus or method described herein, can include one or more of the following features.

In various embodiments, the source can be selected from the group consisting of a flash lamp, a xenon flashlamp, a krypton flash lamp, a xenon-krypton flash lamp, an arc lamp, a diode, and an incoherent light source. In one embodiment, the handpiece includes a coating associated with the nonlinear waveguide for enhancing emission of the electromagnetic radiation.

In some embodiments, the handpiece includes a pump within the system for circulating the fluorescent substance through the nonlinear waveguide. In one embodiment, the handpiece includes a system for cooling the fluorescent substance. The handpiece can include a port adjacent the system, the port in fluid communication with the system and adapted for receiving the fluorescent substance. The handpiece can include a port that is adapted for receiving the fluorescent substance from a reservoir cartridge, the reservoir cartridge detachably connectable with the port.

In certain embodiments, the handpiece includes a reflector adjacent a proximal end of the nonlinear waveguide, the reflector for reflecting light to a distal end of the nonlinear waveguide for delivery to the biological tissue. In one embodiment, the modulated electromagnetic radiation delivered to the biological tissue is substantially fluorescent light. The system can extend the usable lifetime of the fluorescent substance by at least one of mitigating quenching of the fluorescent substance, mitigating bleaching of the fluorescent substance, mitigating heating of the fluorescent substance, and mitigating chemical reaction of the fluorescent substance.

In various embodiments, the handpiece includes a connector adjacent a first portion of the handpiece, for connecting the handpiece to an umbilicus and for receiving energy from a conduit in the umbilicus, the energy for driving the source of electromagnetic radiation. In one embodiment, the connector is adapted to receive a fluorescent substance from the umbilicus and is in fluid communication with the system for circulating the fluorescent substance through the nonlinear waveguide.

In some embodiments, the electromagnetic radiation delivered to the biological tissue can be characterized by a pulse width between about 0.5 ms and about 100 s. In one embodiment, the electromagnetic radiation delivered to the biological tissue is absorbed preferentially by hemoglobin in blood over adjacent skin tissue. A spectrum characterizing the electromagnetic radiation delivered to the biological tissue can matched to an absorption spectrum of at least one of whole blood, hemoglobin, reduced hemoglobin, and oxidized hemoglobin. The electromagnetic radiation delivered to the biological tissue can be characterized by a spot size of about 2 mm or greater.

In certain embodiments, modulating at least one property of the electromagnetic radiation can include varying at least one of a wavelength, fluence, pulse or pulse train width (e.g., duration), and pulse or pulse train shape associated with the electromagnetic radiation. In one embodiment, the electromagnetic radiation delivered to the biological tissue is characterized by an energy density between about 0.1 J/cm2 and about 500 J/cm2.

In various embodiments, the handpiece includes a skin contacting portion adjacent the waveguide for contacting the biological tissue and delivering the electromagnetic radiation to the biological tissue. In one embodiment, the handpiece includes a controller for tuning a pulse width characterizing the electromagnetic radiation delivered to the biological tissue.

In some embodiments, the apparatus includes a port associated with the handpiece and a cartridge containing the fluorescent substance detachably connectable to the port, the cartridge providing the fluorescent substance to the system. In one embodiment, the apparatus includes a reservoir for the fluorescent substance, the reservoir associated with the base unit and in fluid communication with the system, through the umbilicus, for providing the fluorescent substance to the system. The handpiece can be detachable from the umbilicus. The base unit can be detachable from the umbilicus.

In certain embodiments, the method includes treating skin having at least one of a superficial vascular lesion, port wine stain, telangiectasia, small vessel diameter lesion, arterial lesion, capillary lesion, venous lesion, pigmented lesion, tattoo, acne, psoriasis, and vitiligo. In one embodiment, the method includes delivering the electromagnetic radiation to the biological tissue in a train of pulses to gradually heat a region of the biological tissue to be treated. In another embodiment, the method includes delivering the electromagnetic radiation to the biological tissue in a train of pulses to first heat a region of the biological tissue to be treated to a predetermined temperature and second to maintain the region of the biological tissue to be treated at about the predetermined temperature. Modulating at least one property of the electromagnetic radiation can include varying at least one of a wavelength, fluence, pulse or pulse train width, and pulse or pulse train shape associated with the electromagnetic radiation.

Other aspects and advantages of the invention will become apparent from the following drawings and description, all of which illustrate principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DETAILED DESCRIPTION OF THE PREFERRED EMBODIMENT

Figure 1:
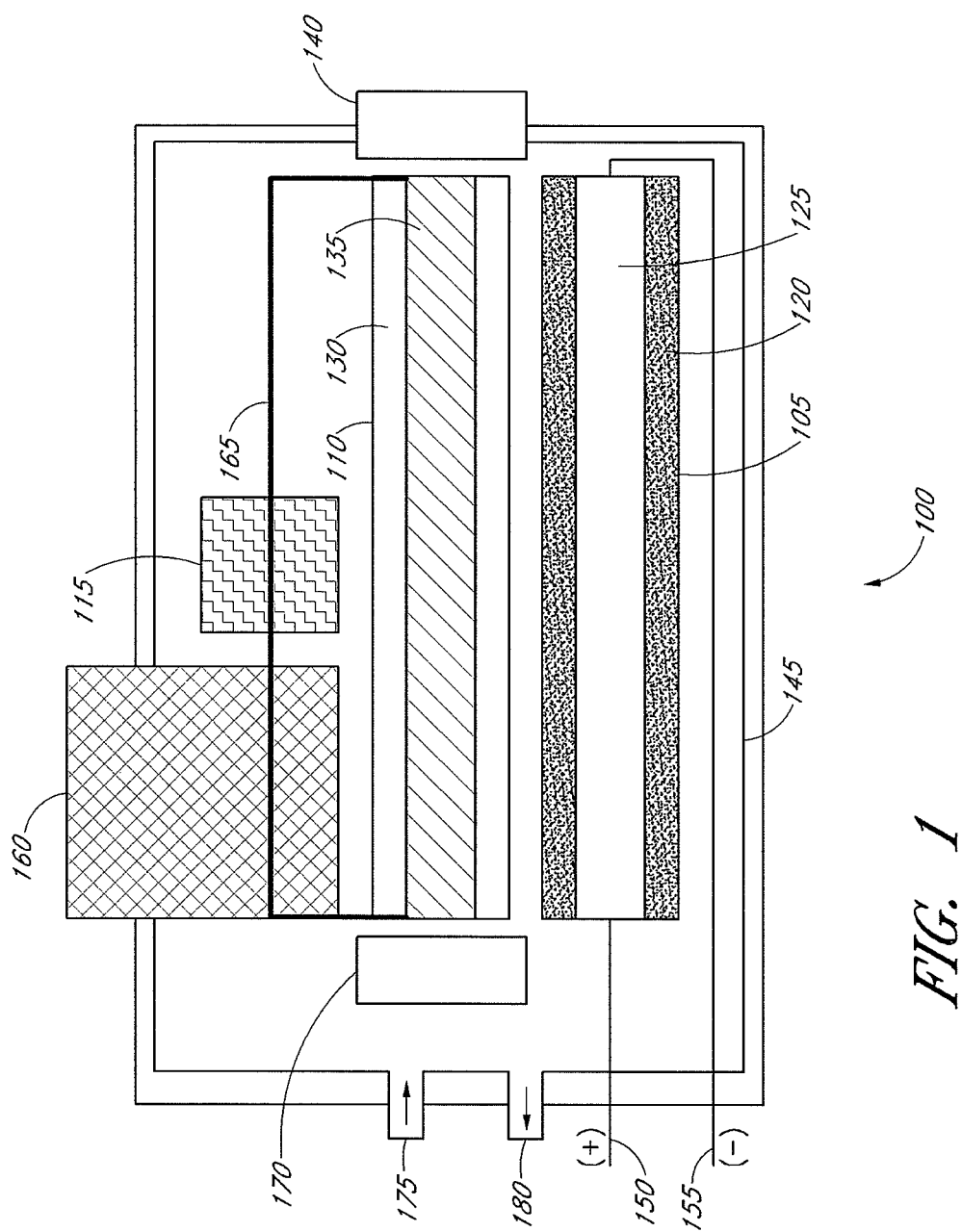
FIG. 1 illustrates various aspects of a fluorescent handpiece.

FIG. 1 illustrates various aspects of a fluorescent handpiece 100 for treating biological tissue using electromagnetic radiation. The handpiece 100 includes a source 105 of electromagnetic radiation and a nonlinear waveguide 110 adjacent the source 105. The source 105 can include a cover 120 and can have a gas in its interior 125. The source 105 can have positive 150 and negative 155 terminals, for establishing a circuit to deliver energy to drive the source 105. The waveguide 110 can include a pipe 130 and a passage 135 for a fluorescent substance. The handpiece 100 can include a system 115 for circulating a fluorescent substance through the waveguide 110. The handpiece 100 can also include a conduit 165 that establishes fluid communication between the waveguide 110, the system 115, and a reservoir 160. Further, the handpiece 100 can include a skin contacting portion 140 adjacent the waveguide 110 and a reflector 170 adjacent a proximal end of the waveguide 110. Furthermore, the handpiece 100 can include cooling system 145 in thermal communication with at least one of the source 105, the waveguide 110, and the system 115. In the illustrated embodiment, the cooling system 145 includes an intake 175 and an exhaust 180, for receiving and removing coolant.

In various embodiments, the source 105 can be a flash lamp, a xenon flashlamp, a krypton flash lamp, a xenon-krypton flash lamp, an arc lamp, a diode, and an incoherent light source. The handpiece 100, in various embodiments, can include one, two, three, or more sources. The waveguide 110 receives electromagnetic radiation from the source 105 and delivers electromagnetic radiation to the biological tissue (not shown). The waveguide 110 can include a glass, plastic, borosilicate, silicate, sapphire, poly methyl methacrylate (PMMA), or any other suitable transparent material. The waveguide 110 can include a coating for enhancing emission of the electromagnetic radiation. For example, the coating can be at least one of a metal, silica, silica-titania, titania, and organic material. In one embodiment, the waveguide 110 is a single tube waveguide adapted for containing a fluorescent substance. In other embodiments, a waveguide can be a coaxial waveguide adapted for separately containing two or more fluorescent substances.

The waveguide 110 can be adapted to deliver electromagnetic radiation directly to the biological tissue, or can be adapted to deliver electromagnetic radiation to the biological tissue through a skin contacting portion 140 adjacent the waveguide 110. The skin contacting portion 140 can include a glass, silica, sapphire, or plastic. The electromagnetic radiation delivered to the biological tissue can be substantially fluorescent light. In various embodiments, the handpiece 100 includes a reflector 170 adjacent a proximal end of the waveguide 110. The reflector 170 is adapted for reflecting light to a distal end of the nonlinear waveguide for delivery to the biological tissue. In one embodiment, the reflector 170 is a mirror. In another embodiment, the reflector 170 is a white (e.g., does not substantially absorb electromagnetic radiation) surface. The reflector 170 can wrap around the waveguide 110 and/or the source 105, to increase the amount of electromagnetic radiation delivered to the waveguide 110. The reflector 170 can be an ellipsis or other geometrical shape selected to focus and/or deliver electromagnetic radiation from the source 105 to the waveguide 110.

Figure 2:
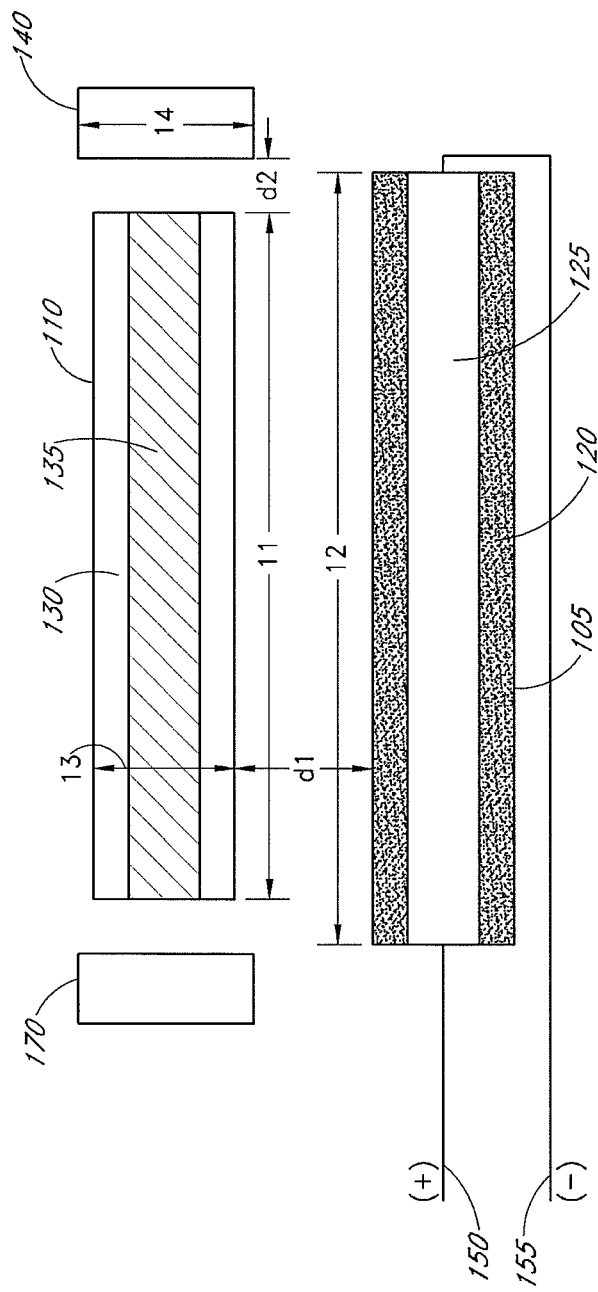
FIG. 2 illustrates an exemplary arrangement of some aspects of a fluorescent handpiece.

FIG. 2 illustrates an exemplary arrangement of various aspects of a fluorescent handpiece. In various embodiments, the waveguide 110 is separated by a distance d1 from the source 105, which can mitigate heating of the waveguide 110 and the fluorescent substance by the source 105 by mitigating the thermal communication between the source 105 and the waveguide 110. The separation distance d1 can also mitigate heating by facilitating a coolant, or other cooling element, to be disposed between the source 105 and the waveguide 110. In one embodiment, distance d1 can be about 10 mm. In various embodiments, the waveguide 110 has a length l1, which can be greater than or equal to the length l2 of the source 105 (e.g., arc length, excluding the dimension of the electrodes), which can facilitate transmission of electromagnetic radiation to substantially the entire length of the waveguide 110 and/or maximize the use of the fluorescent substance. In one embodiment, length l1 can be about 1 mm shorter than the length l2 (e.g., 0.5 mm shorter at each end). In various embodiments, the waveguide 110 is separated by a distance d2 from the skin contacting portion 140. In one embodiment, the distance d2 is about 0.5 mm. In various embodiments, the waveguide 110 has a diagonal length l3 that is less than a corresponding diagonal length l4 of the skin contacting portion 140. In one embodiment, length l4 is about two times distance d2 longer than length l3 (e.g., l4≈2·d2+l3), to direct the cone electromagnetic radiation emitted from waveguide 110 to the skin. However, the lengths l4 and l3 are not limited to this relationship and can be substantially the same, greater, or lesser.

In another embodiment, the waveguide 110 and the skin contacting portion 140 are substantially in contact. In one embodiment, the waveguide 110 and the reflector 170 are not in direct contact or are otherwise separated (e.g., intervened by a gas, liquid, or solid). This separation can facilitate cooling of the waveguide 110, for example, by increasing thermal communication between the waveguide 110 and a coolant or other cooling element. This spatial separation can also be designed to optimize the reflection of electromagnetic radiation from a proximal end of the waveguide 110, to the reflector 170, and back into the waveguide 110. In another embodiment, the waveguide 110 and the reflector 170 are substantially in contact. The relative positions, sizes, and/or optical properties (e.g., convexity/concavity) of the waveguide 110 and the reflector 170 can be designed to maximize the amount of electromagnetic radiation reflected back into the waveguide.

The fluorescent substance can be circulated by the system 115 through the waveguide 110, and is capable of modulating at least one property of the electromagnetic radiation. The system 115 can help extend the usable lifetime of the fluorescent substance by at least one of mitigating quenching of the fluorescent substance, mitigating bleaching of the fluorescent substance, mitigating heating of the fluorescent substance, and mitigating chemical reaction of the fluorescent substance. In some embodiments, the system 115 can be adjacent a port, which is in fluid communication with the system and adapted for receiving the fluorescent substance from a reservoir 160. In one embodiment, the port is adapted for receiving the fluorescent substance from a cartridge that is detachably connectable with the port. A cartridge can contain about 2 deciliters, or more, or less, of the fluorescent substance. In other example, the port can be adapted for receiving the fluorescent substance from another source such as an umbilicus that can be attached to the handpiece 100. A conduit 165 establishes a fluid communication between the waveguide 110, the system 115, and the port.

The system 115 can include a pump for circulating the fluorescent substance. The pump can be any type of pump suitable for a fluorescent substance, including a bellows, centrifugal, diaphragm, drum, flexible liner, flexible impeller, gear, peristaltic (e.g., tubing), piston, progressive cavity, rotary lobe, rotary vane, or syringe pump. In one embodiment, the pump is a magnetically-coupled gear-type pump. In another embodiment, the pump is a solenoid operated pump. In various embodiments, the pump can include a polytetrafluoroethylene (PTFE, for example TEFLON®, a registered trademark of E. I. du Pont de Nemours and Company) or a stainless steel material defining at least a portion of a circulation path of the fluorescent substance. PTFE, or a material with similar physical and chemical properties, can be used in the seals. Pump materials can be selected that are essentially chemically inert, for example, with respect to the fluorescent substance and the operating environment.

Figure 3:
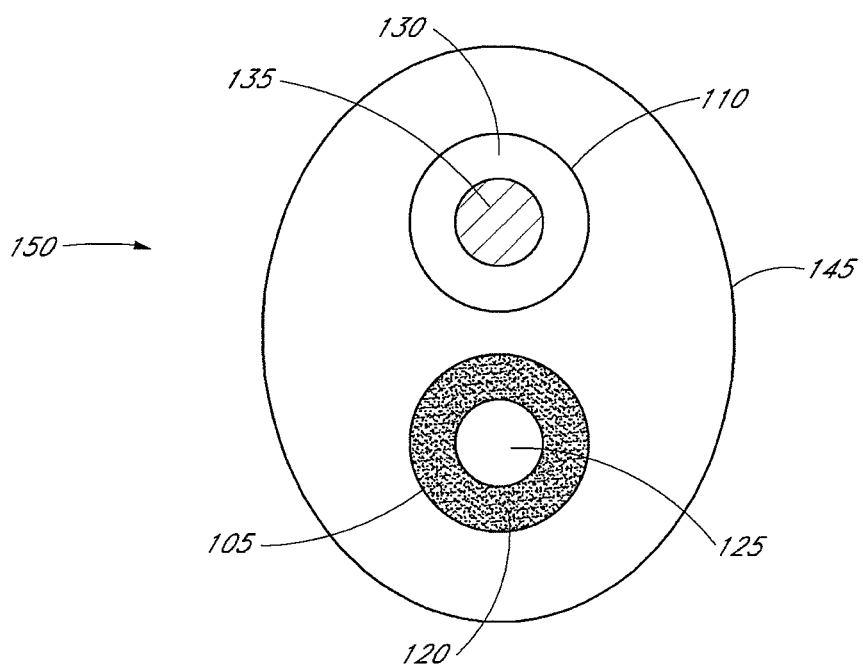
FIG. 3 illustrates another view of certain aspects of a fluorescent handpiece.

FIG. 3 illustrates a cross sectional view 150 of a portion of the fluorescent handpiece of FIG. 1. The source 105 can include a cover 120 and can have a gas in its interior 125. In one example, the gas is xenon. In general, the source 105 is selected to emit at least a wavelength of light employed by the fluorescent substance. In one embodiment, the passage 135 through the waveguide 110 has a diameter of about 2 mm. In one embodiment, the thickness of the pipe 130 wall can be about 0.5 mm. In general, the passage 135 has a diameter is selected to contain a sufficient volume of fluorescent substance, the thickness of the pipe 130 wall is selected based upon the material to provide sufficient structural integrity, and the total diameter of the waveguide 110 is chosen with regard to the desired spot size to be produced by the handpiece 100.

In general, the fluorescent substance is capable of modulating (e.g., transforming, converting, or varying) at least one property of the electromagnetic radiation. For example, the fluorescent substance can be a dye selected to convert the electromagnetic radiation from at least one first wavelength to at least one second wavelength. In some embodiment, more than one dye can be employed to utilize the light from the source 105. Accordingly, at least one dye can be selected depending upon the desired treatment and/or desired emission wavelength. Because the emission wavelength can be controlled by selecting one or more appropriate dyes, the fluorescent handpiece 100 does not require a filter to obtain the desired emission wavelength. However, in some embodiments, the fluorescent handpiece 100 can include a filter for controlling the wavelengths delivered to the biological tissue.

The absorbing and emitting wavelengths of the fluorescent substance can be selected by the user or a technician. In one example, the fluorescent substance can change blue-green light to yellow light. For example, the fluorescent substance can be a liquid dye such as pyrromethene, preferably pyrromethene 580, for changing light emitted from the source 105 to the desired wavelength. A suitable concentration can be a concentration sufficient to achieve about 100% absorption of electromagnetic radiation. The liquid base can be, for example, an alcohol or a mixture of alcohols, preferably methanol and/or ethanol. In various embodiments, the fluorescent substance can include 4-dicyanomethylene-2-methyl-6-(p(dimethylamino)styryl)-4H-pyran (DCM), pyrromethene, fluorescein, coumarin, stilbene, umbelliferone, tetracene, malachite green, rhodamine, or rhodamine 6G. In various embodiments, adamantane can be added to a fluorescent substance to prolong its life. In some embodiments, cycloheptatriene and cyclooctatetraene can be added to a fluorescent substance as triplet quencher, to increase output power. In certain embodiments, a fluorescent substance can include one or more pyrromethenes. The reflection index for the liquid can differ strongly from the reflection index in the waveguide 110. One suitable flow rate for the liquid can be about 4 L/min. The passage 135 can be part of the system 115.

In various embodiments, the cooling system 145 can be a system for cooling the fluorescent substance. In some embodiments, the system 115 for circulating a fluorescent substance can function as, or include a, system for cooling the fluorescent substance. The cooling system 145 can also be adapted to cool any of the components of the handpiece 100, and/or to cool the biological tissue. The cooling system 145 can be in thermal communication with at least one of the source 105, the waveguide 110, the skin contacting portion 140, and the system 115. The cooling system 145 can employ a coolant such as a gas or liquid to cool at least one of the source 105, the waveguide 110, the skin contacting portion 140, and the system 115. In one embodiment, the cooling system 145 employs water as a coolant. In one embodiment, the cooling system 145 has an intake 175 and an exhaust 180, for receiving and removing coolant in the cooling system 145. In one embodiment, the cooling system 145 includes a Peltier, or thermo-electric cooler. The cooling system 145 can include a radiator.

U.S. Pat. No. 5,320,618, the disclosure of which is incorporated herein by reference in its entirety, teaches various sources, waveguides, systems, systems for cooling, and other aspects that can be readily adapted by one skilled in the art for use with the present invention.

In various embodiments, the electromagnetic radiation delivered to the biological tissue is characterized by a pulse width between about 0.5 ms and about 100 s. In some embodiments, a pulse width is between about 5 ms and about 50 ms. In some embodiments, a pulse width is about 1, 2, 3, 4, 5, 10, 15, or 20 s. The electromagnetic radiation delivered to the biological tissue can be absorbed preferentially by a chromophore in the skin. For example, the chromophore can include at least one of hemoglobin in blood, melanin, porphyrin, exogenous pigment, and water in the skin. The chromophore can absorb the electromagnetic radiation preferentially over adjacent skin tissue. The spectrum characterizing the electromagnetic radiation delivered to the biological tissue can be matched to an absorption spectrum of at least one of whole blood, hemoglobin, reduced hemoglobin, and oxidized hemoglobin.

Electromagnetic radiation can also be delivered by scattering and depth-determined deposition. For example, freckles of different shades (e.g., light, medium, and dark relative to surrounding skin) can be treated by different wavelengths of electromagnetic radiation (e.g., about 480 nm for light, about 515 nm for medium, and about 535 nm for dark). A light freckle may not have enough pigment to absorb enough electromagnetic radiation to be effectively treated. By using a shorter wavelength, electromagnetic radiation can scatter more and penetrate less through the freckle, which can result in a longer path and more absorption within the freckle. In another example, a thicker, deeper (e.g. germal) blood vessel can be treated by a relatively longer wavelength, which can reach within the dermis, and a thinner, shallower blood vessel can be treated by a relatively shorter wavelength. In one embodiment, a thicker vessel can be treated by electromagnetic radiation of about 560 to 800 nm and a thinner vessel can be treated by electromagnetic radiation of about 520 to 800 nm.

The electromagnetic radiation delivered to the biological tissue can be characterized by a spot size between about 1 mm and about 20 mm. A spot size can be up to about 1, 2, 3, 4, or 5 mm in diameter. In various embodiments, the handpiece can produce a spot size of about 2 mm or greater in diameter. In general, the optical diameter of the waveguide and the skin contacting portion are proportional to the diameter of the spot size when the skin contacting portion is in contact with the skin.

The electromagnetic radiation delivered to the biological tissue can be characterized by an energy density between about 0.1 J/cm2 and about 500 J/cm2. In various embodiments, the electromagnetic radiation delivered to the biological tissue can be characterized by an energy density between about 1 and about 100 60 J/cm2, about 2.5 J/cm2 and about 60 J/cm2, or about 2.5 J/cm2 and about 12 J/cm2. In certain embodiments, the energy density can be about 1, 5, 10, 50, 100, 150, 200, 250, 300, 350, 400, or 450 J/cm2. The handpiece can include means for tuning a pulse width characterizing the electromagnetic radiation delivered to the biological tissue.

Figure 4:
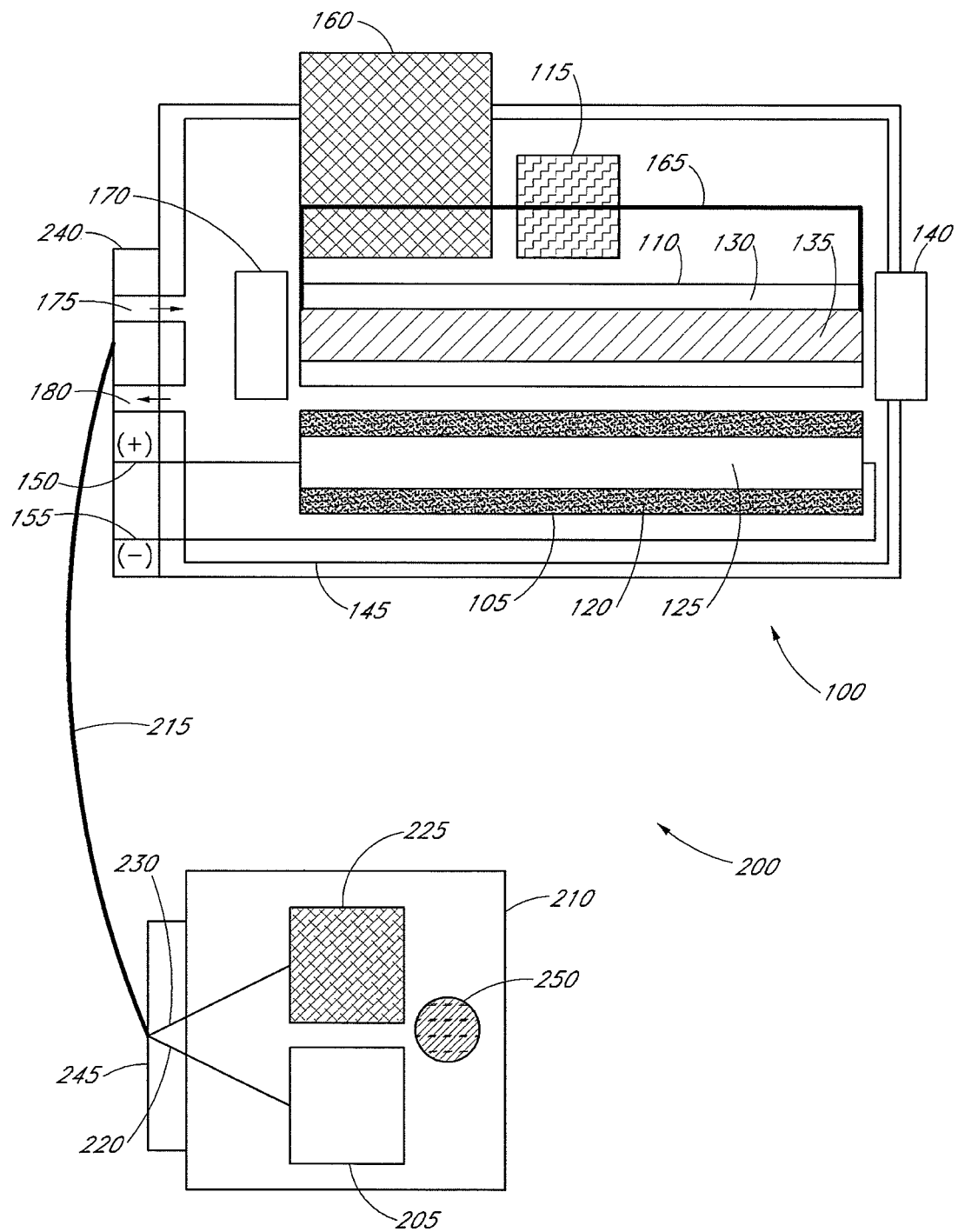
FIG. 4 illustrates an embodiment of an apparatus for treating biological tissue.

FIG. 4 illustrates an embodiment of an apparatus 200 for treating biological tissue. The apparatus 200 includes a fluorescent handpiece 100 that can include the features described in connection with FIG. 1. The apparatus 200 also includes a base unit 210 that can include at least one of an energy 205 source, a coolant 225 source, and a controller 250. The base unit 210 can be connected to the fluorescent handpiece 100 by an umbilicus 215. The umbilicus 215 includes a first 240 point of connection between the umbilicus 215 and the handpiece 100, and a second 245 point of connection between the umbilicus 215 and the base unit 210. The umbilicus 215 can include a power 220 conduit for transmitting energy from the energy 205 source to the source 105 of electromagnetic radiation via a circuit established through the positive 150 and negative 155 terminals. The umbilicus 215 can also include a coolant 230 conduit that establishes coolant communication between the fluorescent handpiece 100 and the base unit 210.

In various embodiments the cooling system 145 can cool the fluorescent substance and/or other components of the handpiece 100. The cooling system 145 can be adapted for cooling biological tissue. The base unit 210 can include a coolant 225 source that can deliver coolant to the cooling system 145 through a coolant 230 conduit. The coolant 230 conduit travels through (or along or on the outside of) the umbilicus to the cooling system 145 via a delivery or circulatory system established through the intake 175 and, if necessary, an exhaust 180. In some embodiments the coolant 230 conduit facilitates coolant flow only to (e.g., in the case of a gas that can be vented) or both to and from (e.g., in the case of a fluid that can be circulated) the handpiece 100. In certain embodiments, the coolant 225 source includes means to control and/or circulate the coolant, and the coolant 230 conduit and cooling system 145 are simply channels. In one embodiment, the cooling system 145 can control and/or circulate the coolant. In one embodiment, the apparatus 200 includes a radiator or heat exchanger in the handpiece 100 or the base unit 210.

In some embodiments, the apparatus 200 includes a controller 250 for controlling at least one of the energy 205 source, the coolant 225 source, the cooling system 145, and the source 105.

FIG. 4 illustrates a first 240 point of connection between the umbilicus 215 and the handpiece 100, and a second 245 point of connection between the umbilicus 215 and the base unit 210. In some embodiments, these points of connection are essentially fixed at the time of manufacture or assembly and are not detachable without specialized tools. However, in various embodiments, these points of connection are easily and quickly detachable and reattachable without specialized tools. In some embodiments, the first 240 point of connection is detachable and reattachable such that a practitioner or technician can easily and quickly change handpieces in a clinical situation. For example, the apparatus can also include a first connector associated with the second end of the umbilicus and a second connector associated with the handpiece, the second connector detachably connectable to the first connector. In various embodiments, the handpiece includes a connector adjacent a first portion of the handpiece, for connecting the handpiece to an umbilicus and for receiving energy from a conduit in the umbilicus, the energy for driving the source of electromagnetic radiation. The connector can be adapted to receive a fluorescent substance from the umbilicus and is in fluid communication with the system for circulating the fluorescent substance through the nonlinear waveguide. This has the advantage of allowing multiple handpieces to be used with a single base unit 210 and/or single umbilicus 215. Likewise, in some embodiments, the second 245 point of connection is detachable and reattachable such that the base unit is detachable from the umbilicus. U.S. patent application Ser. No. 11/800,663, the disclosure of which is incorporated herein by reference in its entirety, teaches various detachable handpieces and connectors that can be readily adapted by one skilled in the art for use with the present invention.

Figure 5:
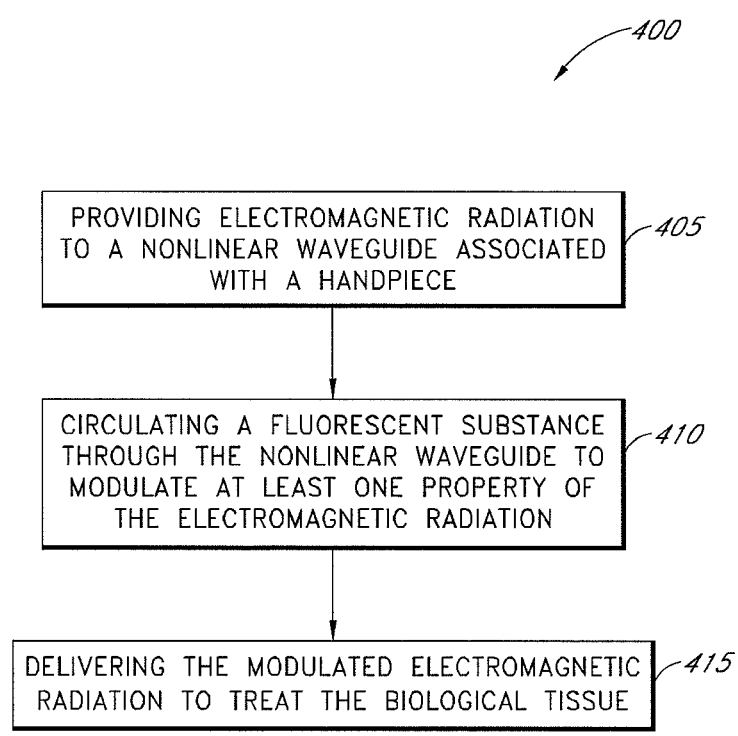
FIG. 5 illustrates a method for treating biological tissue using a fluorescent handpiece.
Figure 6A:
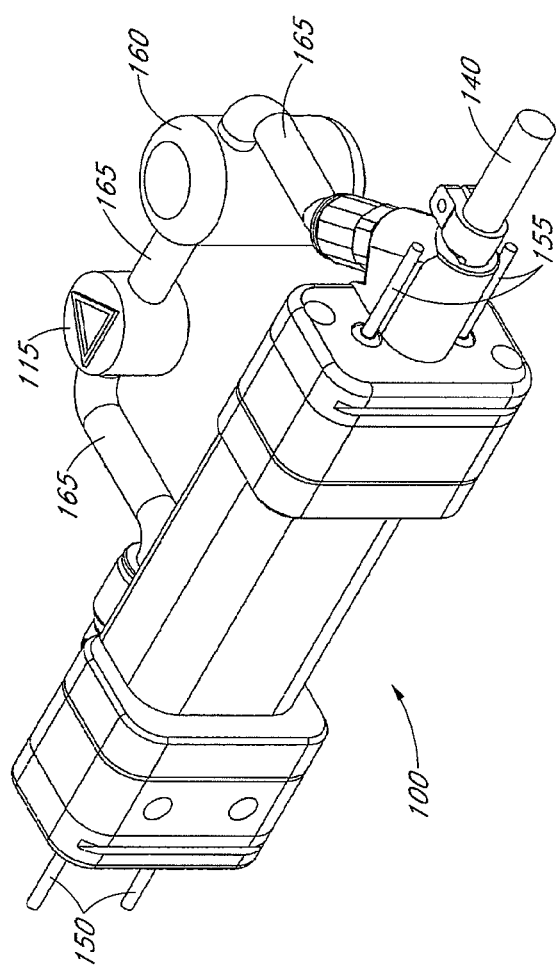
FIGS. 6A-D illustrate the exemplary embodiments of FIGS. 1-4, in 3D renderings produced by CADD-type software.
Figure 6B:
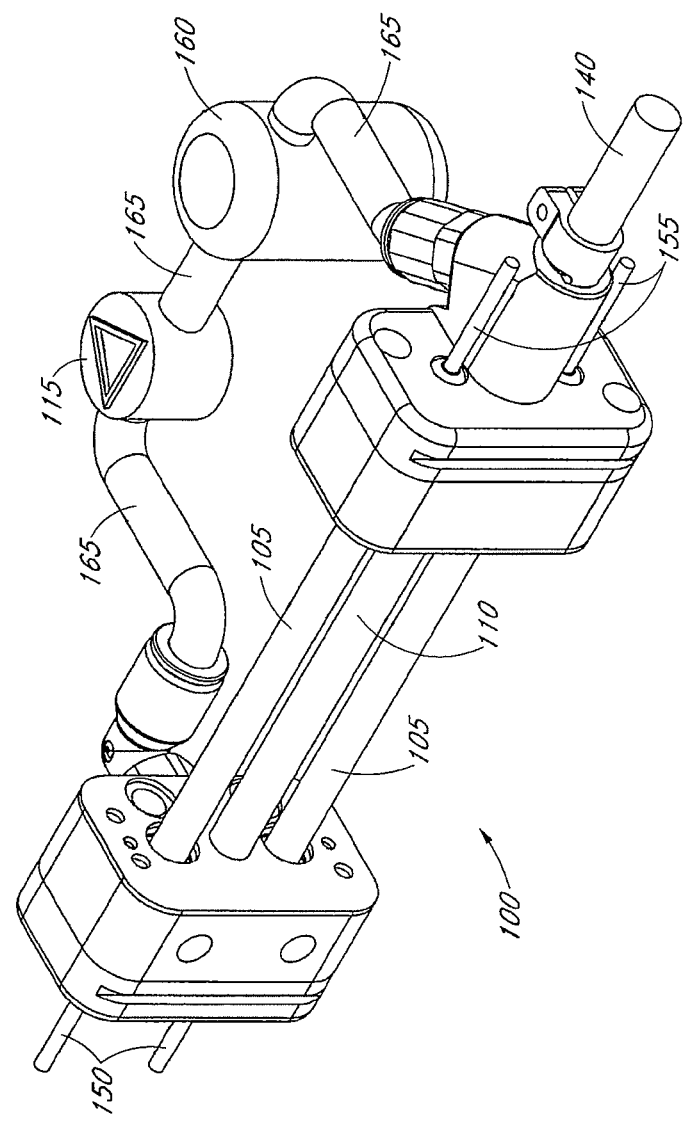
Figure 6C:
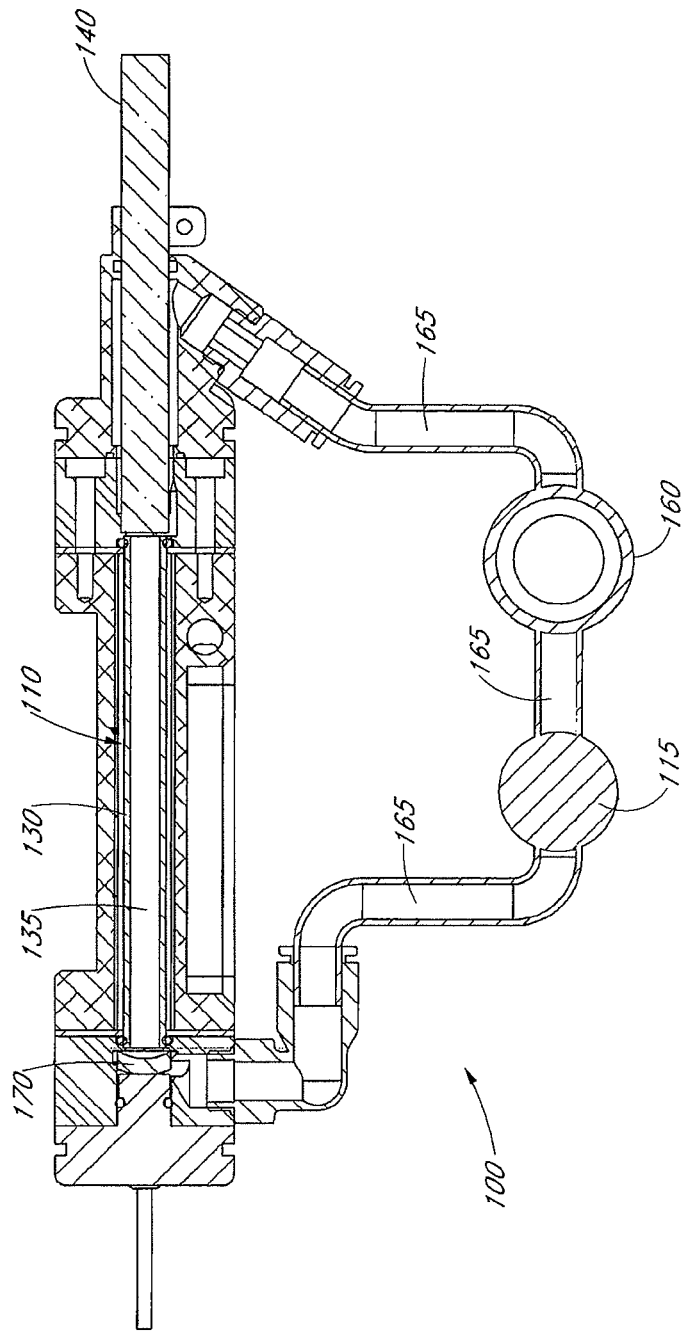
Figure 6D:
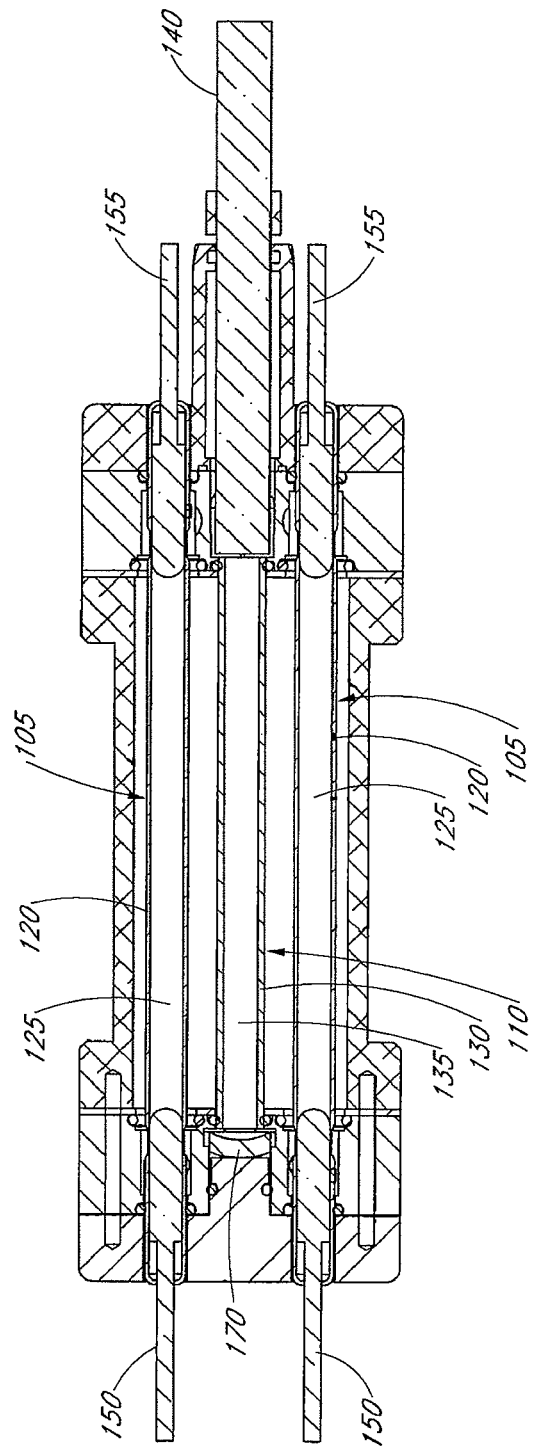

FIG. 5 illustrates a method 400 for treating biological tissue using a fluorescent handpiece. Step 405 includes providing electromagnetic radiation to a nonlinear waveguide associated with a handpiece. The handpiece can include aspects described in connection with FIGS. 1-4. Step 410 includes circulating a fluorescent substance through the nonlinear waveguide to modulate at least one property of the electromagnetic radiation. Modulating at least one property of the electromagnetic radiation can include varying at least one of a wavelength, fluence, pulse or pulse train width, and pulse or pulse train shape associated with the electromagnetic radiation. Step 415 includes delivering the modulated electromagnetic radiation to treat the biological tissue.

In some embodiments, the method 400 includes treating skin having at least one of a superficial vascular lesion, port wine stain, telangiectasia, small vessel diameter lesion, arterial lesion, capillary lesion, venous lesion, pigmented lesion, tattoo, acne, psoriasis, and vitiligo. The method 400 can also include treatments for wrinkles, for skin rejuvenation, for hair removal, and for hair regrowth. In certain embodiments, the method 400 includes delivering the electromagnetic radiation to the biological tissue in a train of pulses to gradually heat a region of the biological tissue to be treated.

FIGS. 6A-D illustrate the exemplary embodiments of FIGS. 1-4, in 3D renderings produced by CADD-type software. The reference numbers in FIGS. 6A-D correspond to the elements discussed in connection with FIGS. 1-4.

While the invention has been particularly shown and described with reference to specific embodiments, it should be understood by those skilled in the art that various changes in form and detail may be made without departing from the spirit and scope of the invention as defined by the appended claims.

What is claimed is:

1. An apparatus for treating biological tissue, comprising:
   a base unit, the base unit comprising an energy supply;
   a handpiece;
   an umbilicus having a first end configured to be coupled to the base unit and a second end configured to be coupled to the handpiece;
   a source of electromagnetic radiation, the source of electromagnetic radiation configured to receive energy from the energy supply and generate electromagnetic radiation;
   a waveguide configured to receive the electromagnetic radiation from the source, the waveguide comprising:
      first and second ends, and a wall extending at least partially therebetween, the wall configured to transmit the electromagnetic radiation therethrough;
      a passage extending along a direction between said first and second ends;
      a fluorescent substance flowable within the passage; and
      an inlet and an outlet in fluid communication with the passage;
   an optical output element optically coupled to one of the first and second ends of the waveguide,
   wherein the fluorescent substance is configured to absorb the electromagnetic radiation from the source through the wall and generate fluorescent light in response to the electromagnetic radiation, wherein the waveguide is configured to guide the fluorescent light emitted by the fluorescent substance towards the optical output element by internally reflecting at least a portion of the fluorescent light, and wherein the optical output element is configured to direct the fluorescent light away from the waveguide;
   a fluid conduit in fluid communication with the waveguide's passage and configured to carry the fluorescent substance between the waveguide's passage and a fluid moving system, the fluid moving system adapted to move the fluorescent substance through the fluid conduit and the waveguide's passage; and
   a cooling system configured to cool the fluorescent substance.

2. The apparatus of claim 1, wherein the cooling system comprises a coolant source and a cooling fluid flow path at least part of which is configured to circulate cooling fluid between the waveguide and the source of electromagnetic radiation.

3. The apparatus of claim 2, wherein the coolant source is located in the base unit.

4. The apparatus of claim 2, wherein at least part of the cooling fluid flow path is located in the handpiece.

5. The apparatus of claim 1, wherein the optical output element is adjacent one of the first and second ends of the waveguide.

6. The apparatus of claim 1, wherein the optical output element is configured to deliver the electromagnetic radiation to biological tissue.

7. The apparatus of claim 1, wherein the fluid moving system is configured to circulate the fluorescent substance from the first end to the second through the passage and from the second end back to the first end through the fluid conduit.

8. The apparatus of claim 1, wherein the optical output element is configured to contact biological tissue to be treated in use.

9. The apparatus of claim 1, further comprising a fluid input port, the fluid input port in fluid communication with the fluid conduit and the fluid circulation system and adapted to receive the fluorescent substance.

10. The apparatus of claim 9, further comprising a cartridge configured to detachably connect to the fluid input port and supply the fluorescent substance.

11. The apparatus of claim 9, wherein the fluid input port is configured to receive the fluorescent substance from the umbilicus.

12. The apparatus of claim 1, wherein the source of electromagnetic radiation is located in the handpiece.

13. The apparatus of claim 1, wherein the waveguide is located in the handpiece.

14. The apparatus of claim 1, wherein the waveguide comprises a nonlinear waveguide.

15. The apparatus of claim 1, wherein the optical output element is located in the handpiece.

16. The apparatus of claim 1, wherein the fluid conduit is located in the handpiece.

17. The apparatus of claim 1, wherein the system is configured to extend the usable lifetime of the fluorescent substance by at least one of: mitigating quenching of the florescent substance, mitigating bleaching of the fluorescent substance, mitigating heating of the fluorescent substance, and mitigating chemical reaction of the fluorescent substance.

18. A method of treating biological tissue, comprising:
providing a waveguide, the waveguide configured to receive electromagnetic energy from an electromagnetic energy source, the waveguide comprising:
first and second ends and a wall extending at least partially therebetween, the wall configured to transmit the electromagnetic radiation therethrough;
a passage extending along a direction between said first and second ends;
a fluorescent substance flowable within the passage, the fluorescent substance configured to absorb the electromagnetic radiation and generate fluorescent light in response to the electromagnetic radiation; and
an inlet and an outlet in fluid communication with the passage;
providing an optical output element optically coupled to one of the first and second ends of the waveguide;
providing a fluid conduit in fluid communication with the waveguide's passage;
providing a fluid moving system adapted to move the fluorescent substance through the fluid conduit and the waveguide's passage;
transmitting electromagnetic radiation through the wall to the fluorescent substance within the passage;
guiding at least some of the fluorescent light emitted by the fluorescent substance in response to the electromagnetic radiation through the waveguide towards the optical output element by internally reflecting at least a portion of the fluorescent light;
directing the fluorescent light away from the waveguide with the optical output element;
moving the fluorescent substance through the fluid conduit and the waveguide's passage; and
cooling the fluorescent substance with a cooling system.

19. The method of claim 18, further comprising treating skin having at least one of a superficial vascular lesion, port wine stain, telangiectasia, small vessel diameter lesion, arterial lesion, capillary lesion, pigmented lesion, tattoo, acne, psoriasis, and vitiligo with the fluorescent light.

20. The method of claim 18, further comprising delivering the fluorescent light to the biological tissue in a train of pulses to gradually heat a region to be treated.

* * * * *